United States Patent [19]

Trinci et al.

[11] Patent Number: 5,563,065
[45] Date of Patent: Oct. 8, 1996

[54] CONTROLLING GROWTH OF FILAMENTOUS MICROORGANISMS

[75] Inventors: Anthony P. J. Trinci, Bramhall; Geoffrey D. Robson, Manchester; Marilyn G. Wiebe, Heaton Moor, all of United Kingdom

[73] Assignee: Zeneca Limited, London, England

[21] Appl. No.: 244,859

[22] PCT Filed: Dec. 16, 1991

[86] PCT No.: PCT/GB91/02234

§ 371 Date: Oct. 12, 1994

§ 102(e) Date: Oct. 12, 1994

[87] PCT Pub. No.: WO93/12219

PCT Pub. Date: Dec. 16, 1991

[30] Foreign Application Priority Data

Dec. 12, 1990 [GB] United Kingdom ............... 9027016

[51] Int. Cl.⁶ .................................................. C12N 1/14
[52] U.S. Cl. ................................. 435/254.1; 435/256.3; 435/256.5; 435/256.8; 435/929; 435/933
[58] Field of Search ........................... 435/254.7, 929, 435/256.5, 256.3, 256.8, 254.5, 254.1, 933

[56] References Cited

U.S. PATENT DOCUMENTS

| | | | |
|---|---|---|---|
| 3,937,654 | 2/1976 | Solomons et al. | 426/60 |
| 4,061,781 | 12/1977 | Solomons et al. | 426/60 |
| 4,294,929 | 10/1981 | Solomons et al. | 435/254 |
| 4,400,467 | 8/1983 | Bauer et al. | 435/104 |

OTHER PUBLICATIONS

Kurbackaja, et al: "Effects of different ratios of carbon and nitrogen concentration in medium on growth and toxin–formation in Aspergillus fumigatus Fres.", Microbiology Abstracts A. Industrial and Applied Mircrobiology, vol. 11, No. 11, Nov. 1976, p. 1.

Inch et al: "Growth and Blastopore Formation by Pselomyces Fumosoroseus, a Pathogen of Brown Planthopper (Nilagaravate Lugens)", Transactions Of The British Mycological Society, vol. 87, No. 2, Sep. 1986, pp. 215–222.

Primary Examiner—John W. Rollins
Attorney, Agent, or Firm—Cushman Darby & Cushman, L.L.P.

[57] ABSTRACT

A process for the cultivation in continuous culture of a filamentous microorganism in a culture medium to which are supplied sources of carbon and other appropriate nutrients. The carbon or another nutrient source is supplied in an amount limiting to the growth of the culture and constitutes a limiting nutrient thereto. The development of an unwanted variant of the filamentous microorganism is restricted or delayed by supplying a first nutrient source to the culture as a limiting nutrient, and thus changing the nutrient supply to the culture in a manner such that a second nutrient source replaces the first nutrient source as the limiting nutrient.

9 Claims, 6 Drawing Sheets

CONTROLLING GROWTH OF FILAMENTOUS MICROORGANISMS

This invention relates to a process for the continuous or fed batch cultivation of a filamentous microorganism which is controlled to delay or prevent the development of an undesirable variant in the the culture. In particular the invention relates to a process for the production of a proteinaceous product or a metabolite.

During continuous cultivation of filamentous micro-organisms there is a tendency, particularly after prolonged cultivation, for highly branched colonial variants of the micro-organism to appear. Sometimes these variants appear to a limited extent only and do not significantly affect the overall growth of the culture. In other instances however the variants occur to an increasing extent and can eventually become the main microorganism components of the cultures containing them. This tendency has undesirable consequences for commercial fermentations using filamentous microorganisms, particularly fermentations for the production of proteinaceous compositions where it is often desirable to produce filamentous microorganisms having only limited hyphal branching.

Since 1969 a process has been developed in which a strain of *Fusarium graminearum* (Schwabe) is cultivated in a medium containing wheat starch to produce a proteinaceous product which can be formulated into a high protein food for human consumption. The product of this process has good nutritional properties and can be made into a convincing analogue of fibrous foods such as meat and poultry. This process is described inter alia in GB 1346061; GB 1346062; EP 123434 and by Trinci et al in Chapter 2 of "Microbial Growth Dynamics", edited by R K Poole et al and published by the Society of General Microbiology the contents of which documents are incorporated herein by reference. It is desirable that the cultivation conditions are controlled to produce restricted branching of the filamentous product and to limit the extent to which undesirable colonial variants of the process micro-organism develop in the culture.

We have now developed a means whereby a continuous cultivation of a filamentous microorganism can be controlled to delay or prevent the development of an undesirable variant in the culture.

According to the present invention we provide a process for the cultivation in continuous culture of a filamentous microorganism in a culture medium to which are supplied sources of appropriate nutrients including carbon, are nutrient source being supplied in an amount limiting to the growth of the culture and constituting a limiting nutrient thereto, wherein development of an unwanted variant of the filamentous microorganism is restricted and/or declared by supplying a first nutrient source to the culture as a limiting nutrient and then changing the nutrients supply to the culture in a manner such that a second nutrient source replaces the first nutrient source as the limiting nutrient.

Further according to the present invention we provide a process for the production of a proteinaceous product by cultivation in continuous culture of a filamentous microorganism in a culture medium to which are supplied sources of other appropriate nutrients including carbon. One nutrient source being supplied in an amount limiting to the growth of the culture and constituting a limiting nutrient thereto, and separation of the filamentous microorganism from the culture wherein development of an unwanted variant of the filamentous microorganism is restricted and/or delayed by supplying a first nutrient source to the culture as a limiting nutrient and then changing nutrients supply to the culture in a manner such that a second nutrient source replaces the first nutrient source as the limiting nutrient.

Further according to the present invention we provide a process for the production of a metabolite by cultivation in continuous or fed batch culture of a filamentous microorganism in a culture medium to which are supplied sources of carbon and other appropriate nutrients, the carbon or another nutrient source being supplied in an amount limiting to the growth of the culture and constituting a limiting nutrient there to, and recovery of the metabolite from the filamentous microorganism produced or from the culture medium wherein development of a variant of the filamentous microorganism is restricted and/or delayed by supplying a first nutrient source to the culture as a limiting nutrient and then changing the nutrients supply to the culture in a manner such that a second nutrient source replaces the first nutrient source as the limiting nutrient.

The process of the invention has a wide variety of applications and can be used whenever a fermentation process employing a limiting nutrient is operated for the cultivation of a filamentous microorganism. In particular it may be used to produce a proteinaceous product by the fermentation process described in GB 1346061; GB 1346062 and EP 123434. Any suitable filamentous microorganism may be cultivated to produce the proteinaceous product, for example strains of the genus Fusarium such as *Fusarium graminearum* (Schwabe) which is deposited at the Commonwealth Mycological Institute, Kew, under numbers IMI 145425 and CMI CC No 346,762 and strains of Penicillium notatum *chrysogenum* IMI 138,291. The invention may also be employed in a fermentation process using for example a streptomycete for example Streptomyces coelicolor to produce a metabolite, for example an antibiotic which may be streptomycin.

In the process of the invention the limiting nutrients are suitably chosen according to the fermentation and the circumstances in which it is conducted. In the process a single replacement of limiting nutrient may be employed but preferably the process is conducted with a series of replacements of limiting nutrient at intervals throughout its period of operation. The replacements may involve only two nutrient sources as limiting nutrients but preferably the process is conducted with three or more different nutrient sources being used in turn as the limiting nutrient. Preferably the process is operated with a series of three or more nutrient sources being used as limiting nutrient according to a regular cycle.

The timing of the replacement of one nutrient source by another as limiting nutrient can be chosen in a variety of ways. The growth of the culture can be monitored and one nutrient source can be replaced by another when the variant whose development is to be controlled has developed to a predetermined extent, e.g. when it forms at for example 1% of the microorganism cells present in the culture. Alternatively the growth of cultures of a particular microorganism can be studied in detail to enable predictions about the development of the variant to be controlled to be made. When this has been done satisfactorily replacements of nutrient sources as limiting nutrients may be made at predetermined time intervals.

Suitable nutrient sources for use as limiting nutrient include sources of carbon, for example xylose, maltose, ribose, fructose, sucrose or glucose, magnesium, phosphate and sulphate, and especially if a non nitrogen containing metabolite is to be produced, of nitrogen. Preferably the nutrient source used as the limiting nutrient in any cycle of replacements is not a nutrient which is of primary importance in producing the product of the process such as the nitrogen source in a process for producing a proteinaceous product. Strategies involving changing the carbon source as the growth limiting nutrient may be adopted especially between glucose and fructose.

In any process according to the invention suitable strategies for altering the limiting nutrient on a regular basis during the process depend upon the process and more particularly upon the filamentous microorganism employed in it.

Suitable strategies for altering the limiting nutrient include the following, designed primarily for use in a process for the production of a proteinaceous product by cultivation of a Fusarium strain:
a) a strategy in which the culture is regularly monitored and the limiting nutrient is altered when there is an indication that the microorganism population in the culture has begun to alter unfavourably due to the formation of an undesirable variant. In this strategy three different nutrient sources may be used alternatively as the limiting nutrient as follows:

1. Carbon source, e.g. glucose
2. Magnesium source
3. Phosphate source.

Figure 7:
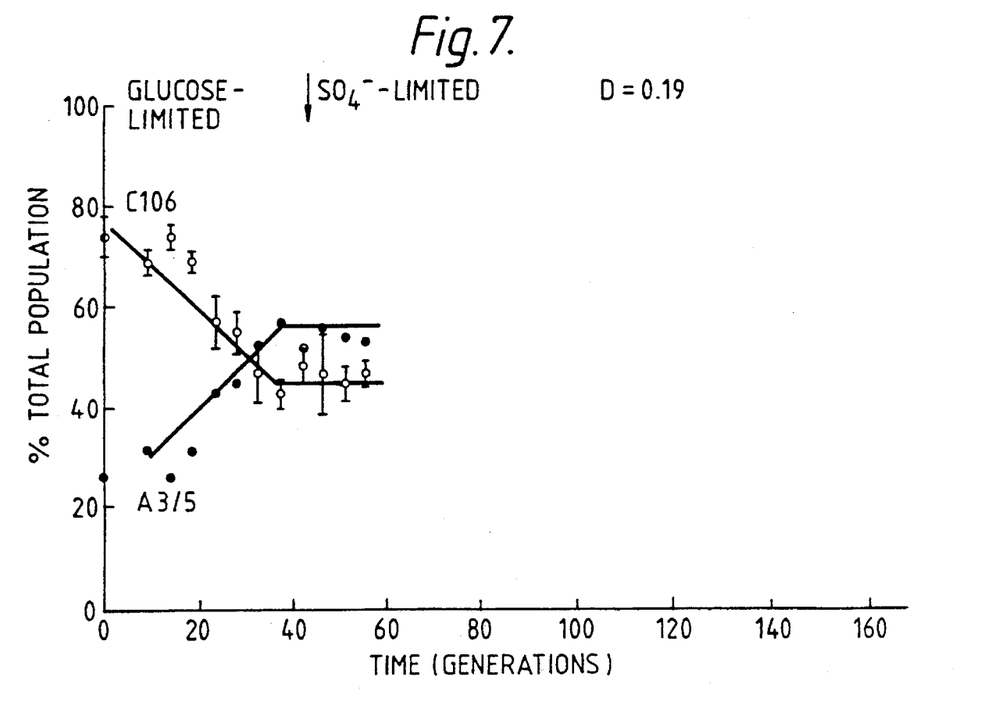

This cycle of limiting nutrients is repeated during the conduct of the process. In a typical instance, using *Fusarium graminearum* (Schwabe) as the microorganism, the time intervals between the limiting nutrient replacements may for example be as follows:

Carbon source to magnesium source—after 20 days

Magnesium source to phosphate source—after 14 days.

b) A preferred strategy for general use in the process of the invention is to alter the nutrient limitation at regular 7 day intervals starting with an initially carbon limited chemostat. The cycle is suitably as follows:

1. Carbon source
2. Magnesium source
3. Phosphate source
4. Sulphate source

A cycle of limiting nutrients repeated throughout the process is a preferred strategy in many instances. It is preferred that the proposed limiting nutrients is not important for the production of the product of the process. It would not for example be a preferred strategy for the production of an antibiotic which sequences sulphate in its synthesis to use sulphate as a limiting nutrient.

During operation of the process of the invention, when a change in limiting nutrient is effected, the dilution rate is suitably decreased, e.g. by an amount in the range 0.05 to 0.10 $hr^{-1}$, in order to remove any undesirable variant from the microorganism population more effectively.

The invention is illustrated by the following Examples:

EXAMPLES

Problem

Generation of a highly branched variant (colonial variant) which supplants of "*Fusarium graminearum*" A 3/5 (the wildtype) (IMI 145425, CMI CC No 346,762) during prolonged continuous culture.

Aim

To develop strategies which will prevent or delay the onset of colonial variant takeover of the culture.

Experimental a) Aim

To study the effects of different nutrient limitations on the ability of colonial variant to displace the wildtype strain during continuous culture. We have used two colonial variants:

i) CCI-1—a variant which arose under carbon limitation in a laboratory fermenter.

ii) C106—a variant which arose during operation of a manufacturing plant.

b) Strategy

We inoculated the fermenter with both wildtype and variant strains to give about 5–40% variant in the population and then grew the mixed culture continuously under a number of nutrient limitations, namely, carbon, ammonia, magnesium and sulphate.

c) Data

Experiments With CCI-1

FIG. 1 shows the CCI-1 variant which was first detected after≈100 generations arising spontaneously in an A 3/5 continuous culture during a glucose-limited fermentation of A 3/5. After a further 100 generations approximately, CCI-1 made up >90% of the total population.

FIG. 2 shows that CCI-1 had a selection coefficient (S) of −0.039 $generation^{-1}$ under magnesium-limitation.

FIG. 3 shows CCI-1 remained approximately constant when grown in ammonia-limited culture.

FIG. 4 shows CCI-1 remained approximately constant when grown in sulphate-limited chemostat culture.

Similarly, CCI-1 takeover could be prevented by switching from glucose-limited medium to fructose=limited medium. CCI-1 increased from 10.6±1.1% of the population to 42.1±4.5% of the population during glucose-limited growth (dilution rate D=0.16 $h^{-1}$). After switching from glucose- to fructose-limited medium the proportion of CCI-1 in the population remained constant at 40.6±2.1%.

It was noted that CCI-1 did not increase in the population in xylose-limited medium (S=−0.06 $generation^{-1}$), although it did increase in maltose-(S=0.09 $generation^{-1}$) and ribose-limited (S=0.09 $generation^{-1}$) medium.

FIG. 5 shows CCI-1 supplanted wildtype A 3/5 when grown in glucose-limited culture (S=0 +0.145 $generation^{-1}$).

FIG. 6 shows how CCI-1 takeover can be prevented. Initially, the culture is under glucose-limitation and CCI-1 begins to supplant the wildtype. After approximately 40 generations, the culture was switched to magnesium-limitation and the increase in CCI-1 was halted. The dotted line shows predicted increase of CCI-1 if glucose-limitation had been maintained.

Experiments with C106

FIG. 7 shows C106 decreased and A 3/5 increased under glucose-limitation (s=−0.02 $generation^{-1}$). After≈40 generations, the culture was switched to sulphate limitation. During sulphate-limited growth, C106 remained at an approximately constant level (S≈45%).

FIG. 8 shows that C106 decreased and A 3/5 increased under ammonia-limitation (S=−0.03 $generation^{-1}$). After≈35 generations, the culture was switched to magnesium-limitation. During magnesium-limited growth, C106 rapidly supplanted the wildtype (S=0.15 $generation^{-1}$). After≈55 generations, the culture was switched to carbon-limitation. After the switch C106 decreased in the population (S=−0.02 generation$^{-1}$, See FIG. 7). During this period, new colonial variants were detected in the population (≈75 generations from start of experiment and 20 generations after the switch from magnesium-to carbon-limitation). These mutants rapidly increased in the population. After≈95 generations, the culture was switched to ammonia-limitation at which point the new colonial variant(s) had attained a level of≈40%. During ammonia-limited growth, the increase in the new colonial variant(s) was halted. C106 also decreased and A 3/5 increased under phosphate-limitation (S=−0.04 generation$^{-1}$).

Figure 9:
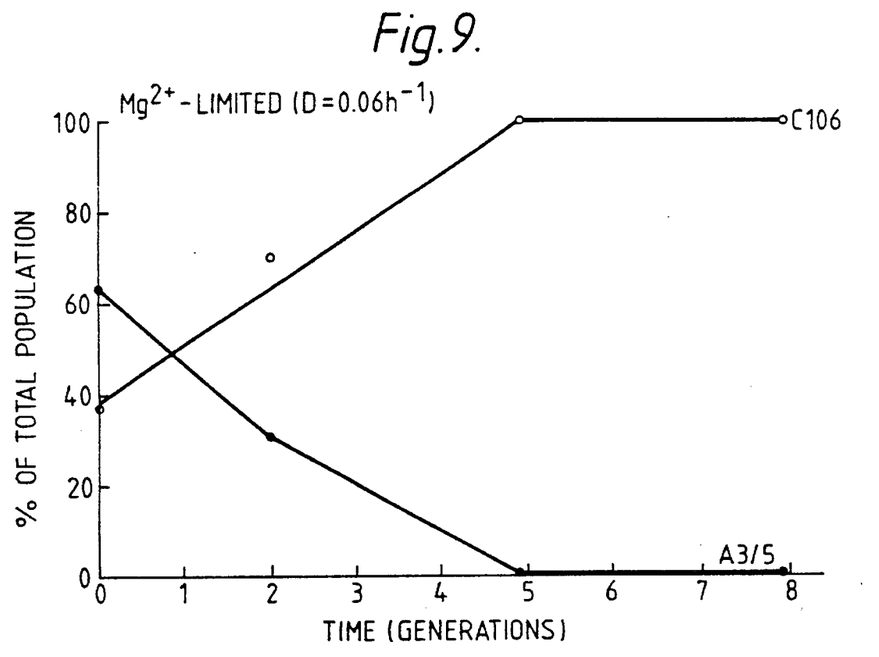
Figure 10:
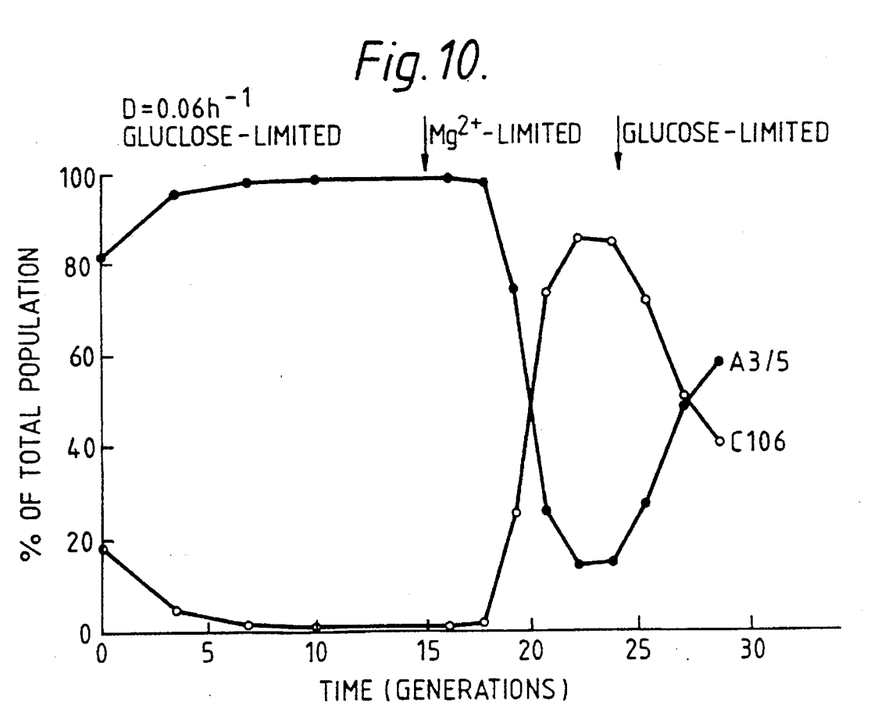

FIG. 9 shows that, under magnesium-limitation at a dilution rate D of 0.06 h$^{-1}$, C106 supplanted the wildtype (S=1.1, generation$^{-1}$, compared to S=0.15 generation$^{-1}$ at D=0.19 h$^{-1}$). In FIG. 10, the wildtype supplanted C106 in glucose-limitation at a dilution rate D of 0.06 h$^{-1}$. After≈15 generations, the culture was switched to magnesium-limitation. During this period, (See FIG. 10) C106 levels rose rapidly (S=1.2 generation$^{-1}$). On switching back to glucose-limitation, C106 levels again fell (≈25 generations).

The compositions of the relevant Vogels media used are shown in the Table below.

This data shows that carbon limitation conditions suppress the population of C106 and are tolerable for long periods in the absence of CCI-1. CCI-1 can be controlled and in some cases reduced by sulphate or magnesium limitation conditions and stabilised under nitrogen limitation conditions. This indicates that by monitoring the variants present and altering the growth limitation conditions appropriately when their population is low it is possible to delay the need to close a manufacturing process down because unwanted organisms have overwhelmed the wanted organisms.

TABLE

Modified Vogel's medium composition

| | glucose ltd (gl$^{-1}$) | NH$_4^+$- ltd | Mg$^{2+}$- ltd | SO4$^-$- ltd | PO4$^-$- ltd |
|---|---|---|---|---|---|
| glucose | 3.0 | 6.0 | 6.0 | 6.0 | 6.0 |
| Na$_3$ citrate | 2.5 | 2.5 | 2.5 | 2.5 | 2.5 |
| KH$_2$ PO$_4$ | 5.0 | 5.0 | 5.0 | 50 | 0.0375 |
| K$_2$SO$_4$ | 0 | 0 | 0 | 0 | 0.16 |
| (NH$_4$)$_2$SO$_4$ | 3.3 | 1.5 | 3.3 | 0 | 3.3 |
| NH$_4$Cl | 0 | 0 | 0 | 1.336 | 0 |
| MgSO$_4$ 7H$_2$O | 0.2 | 0.2 | 0.015 | — | 0.2 |
| MgCl$_2$ 6H$_2$O | — | — | — | 0.2 | — |
| Na$_2$SO$_4$ | — | — | — | 0.02 | — |
| CaCl$_2$ H$_2$O | 0.1 | 0.01 | 0.01 | 0.01 | 0.01 |
| citric acid - 1H$_2$O | 0.005 | 0.005 | 0.005 | 0.005 | 0.005 |
| ZnSO$_4$ 7H$_2$O | 0.005 | 0.005 | 0.005 | 0.005 | 0.005 |
| Fe(NH$_4$)$_2$(SO$_4$)$_2$ 6H$_2$O | 0.001 | 0.001 | 0.001 | 0.001 | 0.001 |
| CuSO$_4$ 5H$_2$O | 0.00026 | 0.00026 | 0.00026 | 0.00026 | 0.00026 |
| MnSO$_4$ H$_2$O | 0.00005 | 0.00005 | 0.00005 | 0.00005 | 0.00005 |
| H$_3$BO$_3$ | 0.00005 | 0.00005 | 0.00005 | 0.00005 | 0.00005 |
| NaMoO$_4$ 2H$_2$O | 0.00005 | 0.00005 | 0.00005 | 0.00005 | 0.00005 |
| Biotin | 0.00005 | 0.00005 | 0.00005 | 0.00005 | 0.00005 |

Experimental Methods

Apparatus: A commercially available continuous fermenter with air and nutrient feed facilities sold by Braun under the trade name Biostat M. (2 liter)

culture volume: 2000 ml medium: modified Vogel's medium (see table)

antifoam: 0.25% (v/v) polypropylene glycol (mixed molecular weight)

pH: maintained at 5.8±0.1 (by addition of 2M NaOH solution)

air pressure: 1.6 l min$^{-1}$ stirrer speed: 1400 rpm temperature: 25° C.

dilution rate: 0.19 h$^{-1}$ (unless otherwise noted)

biomass: approximately 2 g dry weight l$^{-1}$ culture medium (for all limitations).

Assessment of population composition: composition of the population was assessed by making viable counts on agar solidified Vogel's medium. Samples from the fermenter were diluted in sterile distilled water and 0.1 ml of the suspension were spread on 10–15 agar plates to yield 20–60 colonies per plate. Colony forming units (derived from either mycelial fragments or spores) were counted after 72 h incubation at 25° C. Colonial mutant colonies could be distinguished from wild-type colonies because they formed dense colonies which increased slowly in diameter and they were counted separately from the wild-type colonies. Viable counts were made at approximately 24 or 48 h intervals.

Limiting nutrient: stock solutions were prepared as shown in the table. These were limited in one particular nutrient. When switching to a different limiting nutrient a 1–48 hr time interval was required for the levels of the particular nutrient to be reduced as desired in the fermenter vessel, as the nutrient would have been in excess under the previous set of conditions.

Strategies

Figure 1:
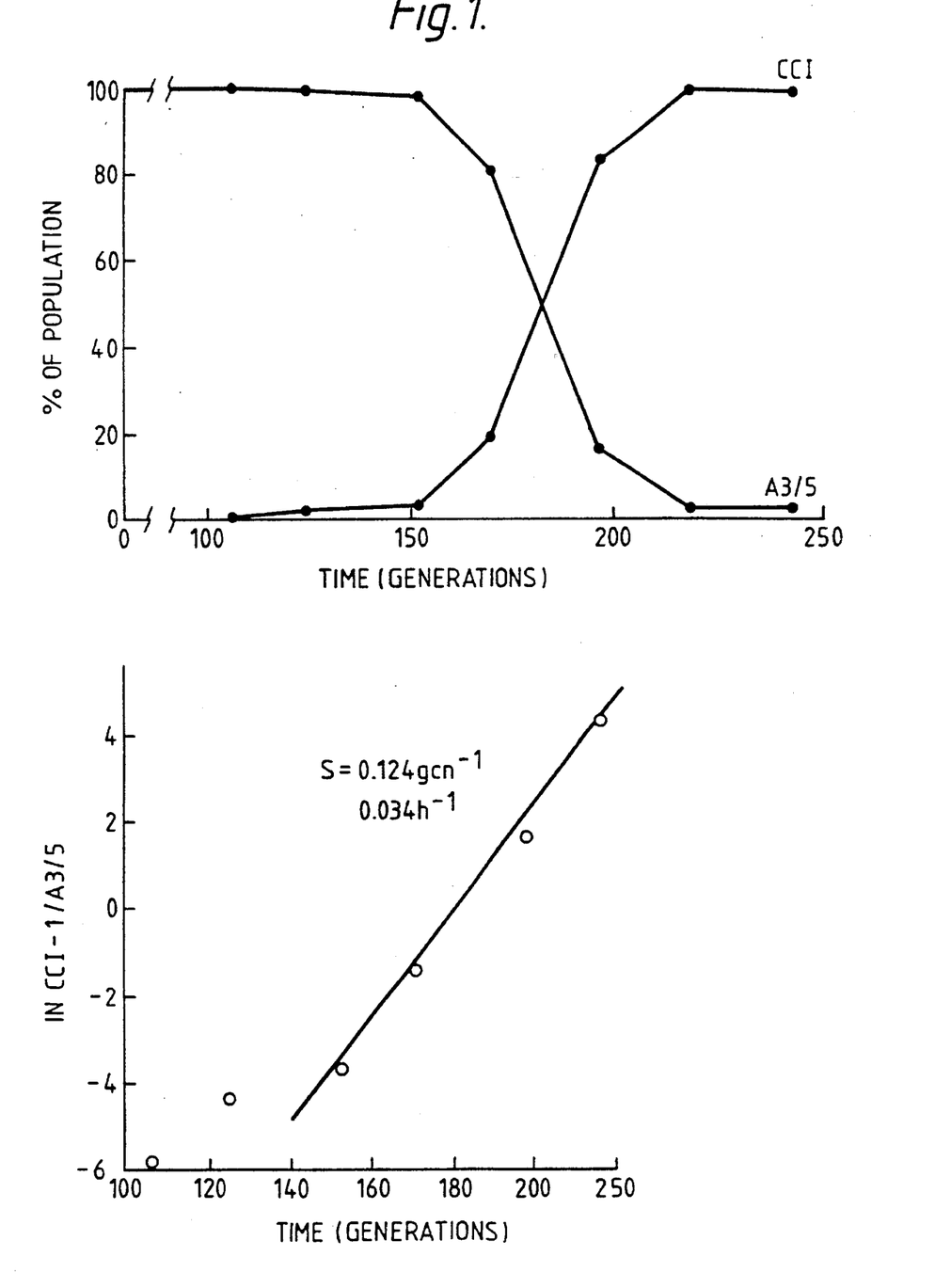
Figure 2:
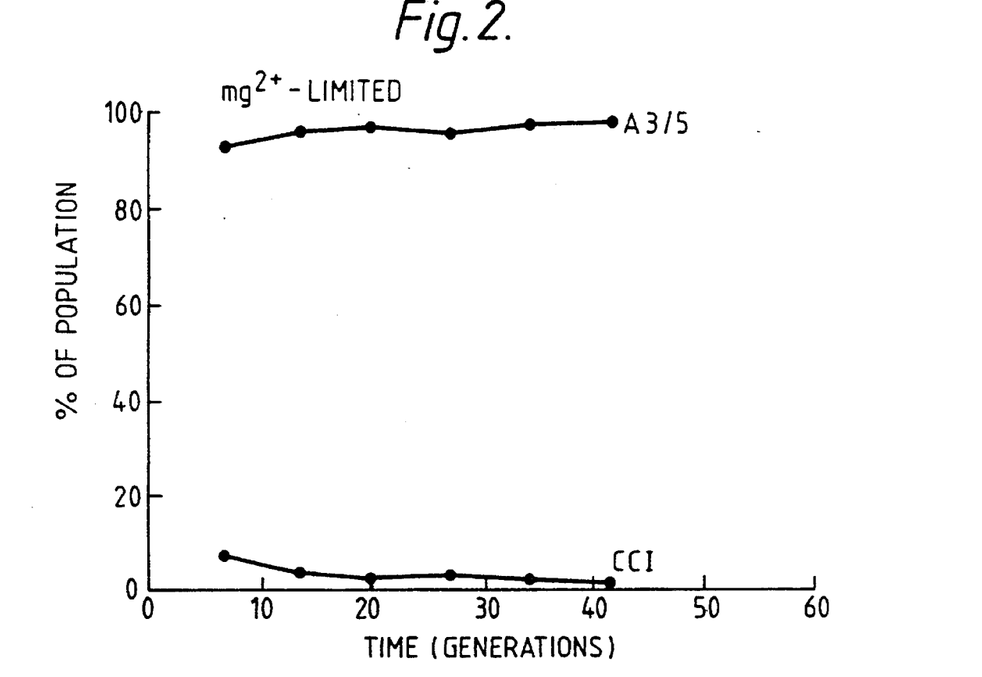
Figure 3:
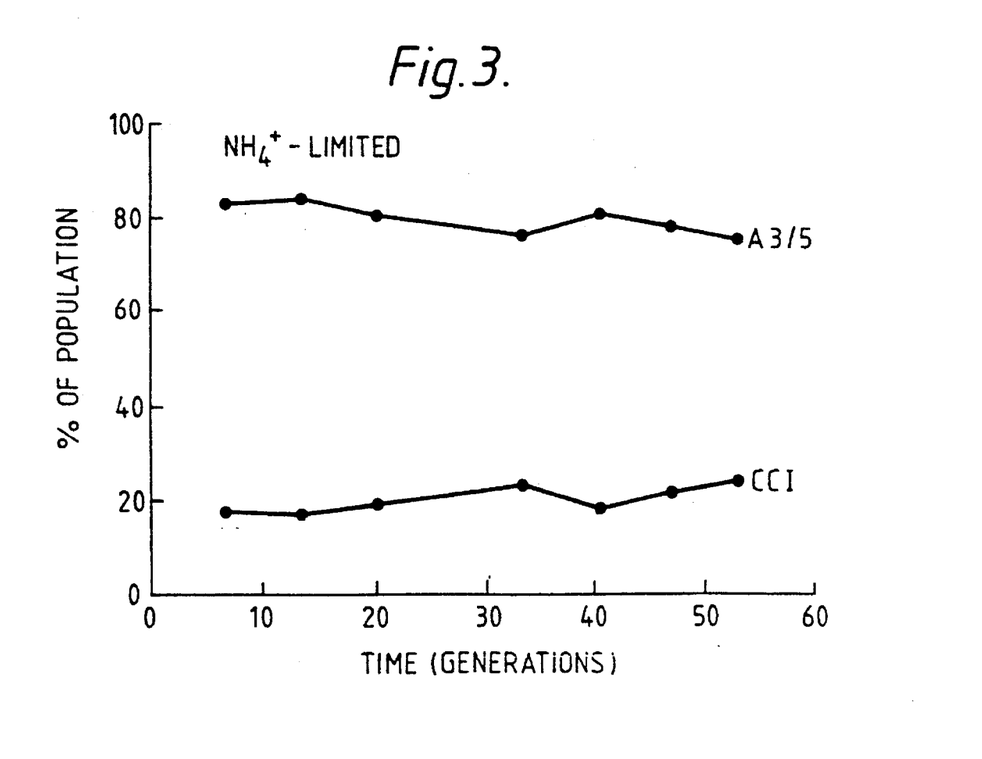
Figure 4:
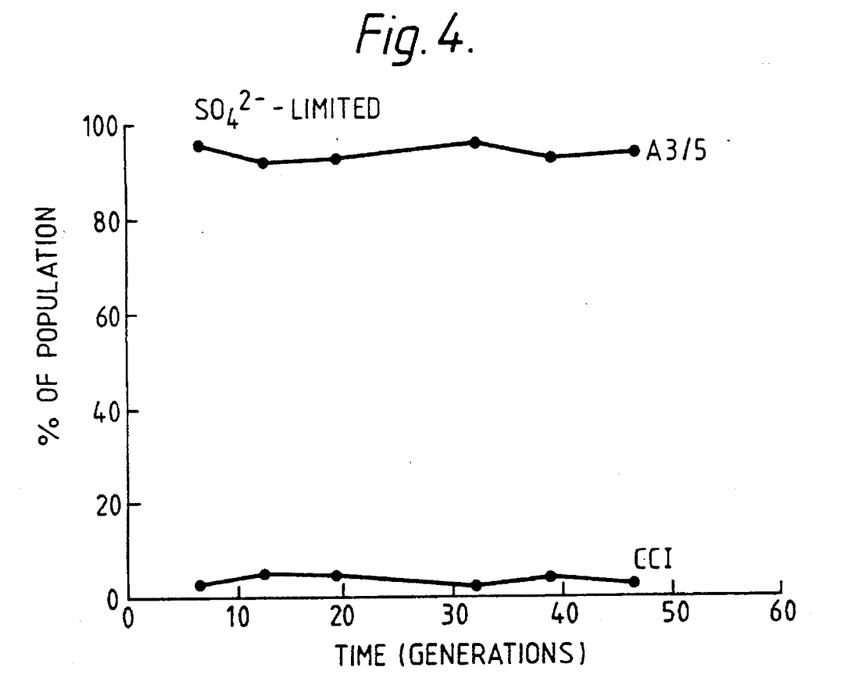
Figure 5:
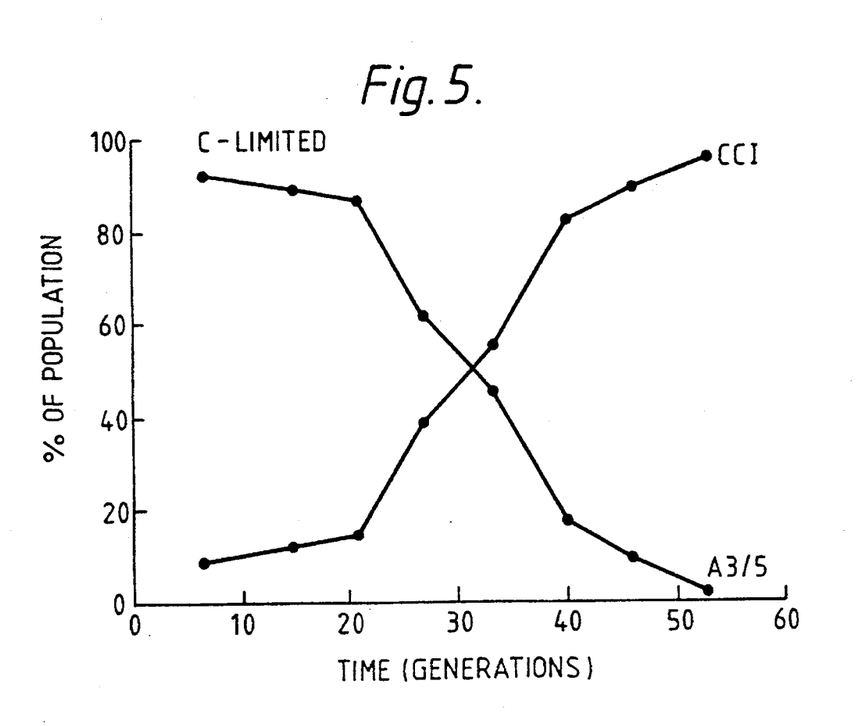
Figure 6:
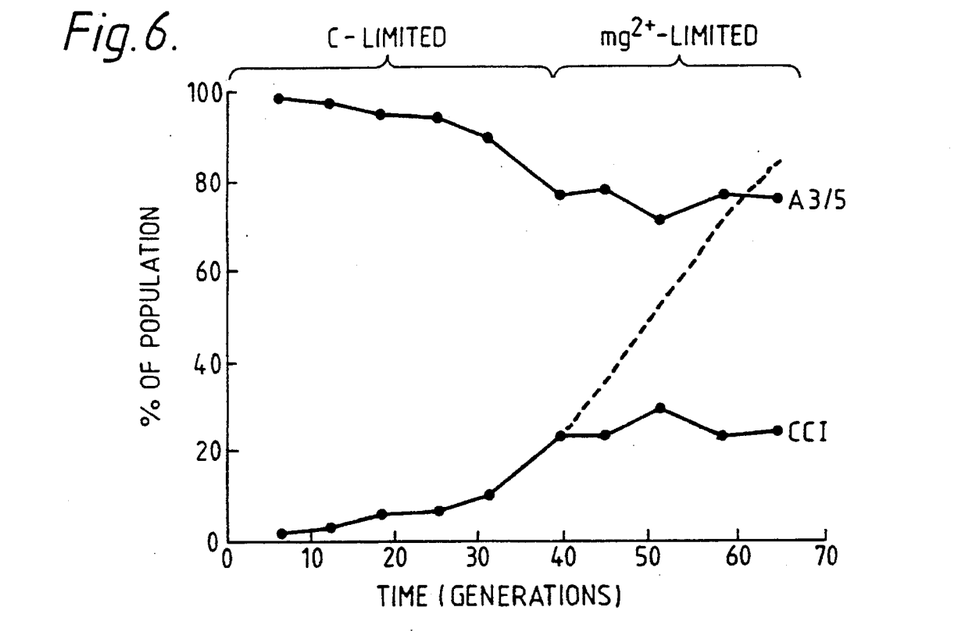
Figure 8:
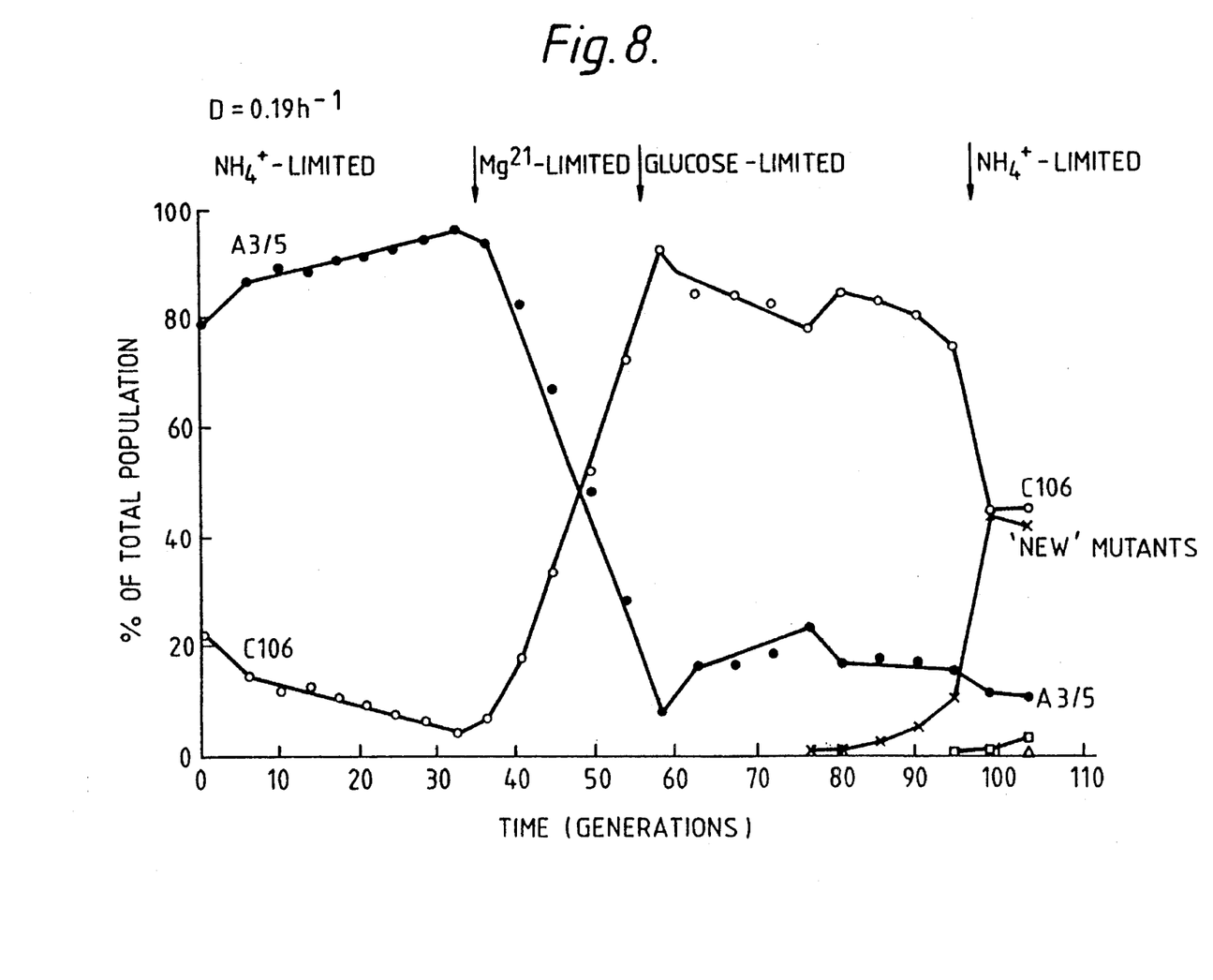

It will be seen from e.g. FIGS. 6 and 8 that the following strategy would be favourable. Alter the nutrient-limitation at the first sign that the population composition has become unfavourable using the following limitations:

a) glucose-limitation for 20 days, after which colonial mutants appear at 1% population b) change to Mg$^{2+}$ limitation for 14 days colonial mutuants now reach 1.5% population c) change to PO$_4$-limitation This procedure keeps the colonial mutant population at below critical levels for a prolonged period.

The change in limitation may be coupled with a temporary decrease in dilution rate to more effectively remove the contaminating mutant from the population. (See for example FIGS. 9 and 10 compared with higher dilution rate in FIG. 8).

An alternative strategy is to alter the nutrient-limitation at regular 7 day intervals as may be seen from FIG. 8.

| The sequence may be, glucose limitation until day 7 | |
|---|---|
| Mg$^{2+}$ | limitation until day 14 |
| PO$_4$— | limitation until day 21 |
| SO$_4$— | limitation until day 28 |
| glucose | limitation until day 35 |
| Mg$^{2+}$ | limitation |
| | and so on |
| glucose | limitation until day 7 |
| Mg$^{2+}$ | limitation until day 14 |
| glucose | limitation |
| | etc | a) is the preferable strategy, but if the process precludes several types of limitation (such as not limiting the nitrogen source in a process producing protein, as not limiting for sulphate in the production of an antibiotic which requires sulphate in its synthesis) then it may be necessary to follow the type of strategy suggested in b).

We claim:

1. A process for the cultivation in continuous culture of a filamentous microorganism in a culture medium to which are supplied sources of carbon and other nutrients, the carbon or another nutrient source being supplied in an amount limiting to the growth of the culture and constituting a limiting nutrient thereto wherein development of a variant of the filamentous microorganism is restricted or delayed by supplying a first nutrient source to the culture as a limiting nutrient and then changing the nutrient supply to the culture such that a second nutrient source replaces the first nutrient source as the limiting nutrient.

2. A process for the production of a proteinaceous product by cultivation in continuous culture of a filamentous microorganism in a culture medium to which are supplied sources of carbon and other nutrients the carbon or another nutrient source being supplied in an amount limiting to the growth of the culture and constituting a limiting nutrient thereto and separation of the filamentous microorganism from the culture wherein development of a variant of the filamentous microorganism is restricted or delayed by supplying a first nutrient source to the culture as a limiting nutrient and then changing the nutrient supply to the culture such that a second nutrient source replaces the first nutrient source as the limiting nutrient.

3. A process for the production of a metabolite by cultivation in continuous culture of a filamentous microorganism in a culture medium to which are supplied sources of carbon and other nutrients the carbon or another nutrient source being supplied in an amount limiting to the growth of the culture and constituting a limiting nutrient thereto and recovery of the metabolite from the filamentous microorganism produced or from the culture medium wherein development of a variant of the filamentous microorganism is restricted or delayed by supplying a first nutrient source to the culture as a limiting nutrient and then changing the nutrient supply to the culture such that a second nutrient source replaces the first nutrient source as the limiting nutrient.

4. A process as claimed in any preceding claim in which the filamentous microorganism is a strain of the genus Fusarium.

5. A process as claimed in any one of claims 1–3 in which after the second nutrient source is used, one or more further different nutrient sources are used in turn as the limiting nutrient.

6. A process according to claim 5 in which the nutrient sources are used as a limiting nutrient according to a regular cycle.

7. A process as claimed in claim 6 in which the replacement of nutrient sources as limiting nutrients is made at predetermined time intervals.

8. A process as claimed in any one of claims 1–3 in which the nutrient sources used as limiting nutrient are selected from carbon, magnesium, phosphate, sulphate and nitrogen.

9. A process as claimed in any one of claims 1–3 in which when a change in limiting nutrient is effected the dilution rate is decreased.

* * * * *